United States Patent [19]
Harris

[11] Patent Number: 5,454,786
[45] Date of Patent: Oct. 3, 1995

[54] CARTRIDGE ASSEMBLY FOR A LYOPHILIZED COMPOUND FORMING A DISPOSABLE PORTION OF AN INJECTOR PEN AND METHOD FOR SAME

[75] Inventor: Dale C. Harris, Fairland, Ind.

[73] Assignee: Eli Lilly and Company, Indianapolis, Ind.

[21] Appl. No.: 218,653

[22] Filed: Mar. 28, 1994

Related U.S. Application Data

[62] Division of Ser. No. 31,683, Mar. 15, 1993, Pat. No. 5,334,162.

[51] Int. Cl.$^6$ .......................... A61M 37/00; A61M 5/32; A61B 19/00
[52] U.S. Cl. .............................. 604/88; 604/92; 604/411; 604/416
[58] Field of Search ................... 604/82, 92, 411, 604/414, 415, 416, 905, 403, 88; 141/329, 330, 332, 333, 334, 383, 386, 27

[56] References Cited

U.S. PATENT DOCUMENTS

| | | | |
|---|---|---|---|
| 1,459,485 | 6/1923 | Whitney | 141/332 |
| 2,085,392 | 6/1937 | Reichel | 604/415 |
| 2,347,737 | 5/1944 | Fuller | 220/367 |
| 2,647,513 | 8/1953 | Holmes | 604/415 |
| 2,870,766 | 1/1959 | Dann et al. | 604/232 |
| 3,002,517 | 10/1961 | Pitton | 132/85 |
| 3,080,866 | 3/1963 | Friedman | 604/88 |
| 3,292,342 | 12/1966 | Kapeker | 53/101 |
| 3,387,609 | 6/1968 | Shields | 215/247 |
| 3,416,657 | 12/1968 | Sorensen, Jr. et al. | 604/92 |
| 3,976,069 | 8/1976 | Ong | 604/232 |
| 4,392,492 | 7/1983 | Pick | 604/82 |
| 4,413,760 | 11/1983 | Paton | 222/309 |
| 4,592,745 | 6/1986 | Rex et al. | 604/211 |
| 4,710,179 | 12/1987 | Haber et al. | 604/211 |
| 4,723,945 | 2/1988 | Theiling | 604/232 |
| 4,735,608 | 4/1988 | Sardam | 604/82 |
| 4,865,591 | 9/1989 | Sams | 604/186 |
| 4,883,472 | 11/1989 | Michel | 604/208 |

(List continued on next page.)

FOREIGN PATENT DOCUMENTS

| | | |
|---|---|---|
| 0268191 | 11/1987 | European Pat. Off. . |
| 0293572 | 4/1988 | European Pat. Off. . |
| 0327910 | 1/1989 | European Pat. Off. . |
| 0528120 | 2/1993 | European Pat. Off. . |
| 3840000 | 7/1989 | Germany . |
| WO87/02895 | 5/1987 | WIPO . |
| WO88/07874 | 10/1988 | WIPO . |
| WO-A-8904676 | 6/1989 | WIPO . |

OTHER PUBLICATIONS

Bedienungsanleitung, 1990, Instruction Booklet for Use of Optipen.

*Primary Examiner*—C. Fred Rosenbaum
*Assistant Examiner*—Frank Wilkens, III
*Attorney, Agent, or Firm*—Baker & Daniels

[57] ABSTRACT

A cartridge assembly for holding a lyophilized product, forming a disposable portion of a pen injector includes a cylindrical glass cartridge adapted to receive the product, a closure cap, a cartridge case, and a plunger mechanism. The closure cap is adapted to retain an elastomeric disc seal during lyophilization and includes diametrically opposed ledges. The closure cap and seal are adapted to cover a neck portion of the ampule, the neck portion having on its end a radially extending circumferential flange. The ledges of the closure cap and the flange of the neck portion allow the closure cap to remain open during lyophilization, oxygen purge and nitrogen overlay. An oval-shaped indentation formed on the inside of the closure cap aids in snapping the closure cap about the flange without crimping to retain the closure cap underneath the flange. Reconstitution of the lyophilized drug is accomplished without foaming by use of an obliquely angled connector which causes the diluent to indirectly impinge on the drug. The injection pen and cartridge assembly cooperate such that the length of travel of the plunger rod during retraction is less than the axial length of a recess in the rod tip.

5 Claims, 5 Drawing Sheets

U.S. PATENT DOCUMENTS

| | | | |
|---|---|---|---|
| 4,936,833 | 6/1990 | Sams | 604/232 |
| 4,944,736 | 7/1990 | Holtz | 604/415 |
| 4,973,318 | 11/1990 | Holm et al. | 604/208 |
| 5,069,670 | 12/1991 | Vetter et al. | 604/82 |
| 5,071,017 | 12/1991 | Stull | 215/247 |
| 5,084,040 | 1/1992 | Sutter | 604/415 |
| 5,088,612 | 2/1992 | Storar et al. | 215/247 |
| 5,100,010 | 3/1992 | Waters | 215/248 |
| 5,247,972 | 9/1993 | Tetreault | 141/386 |
| 5,360,410 | 11/1994 | Wacks | 604/415 |

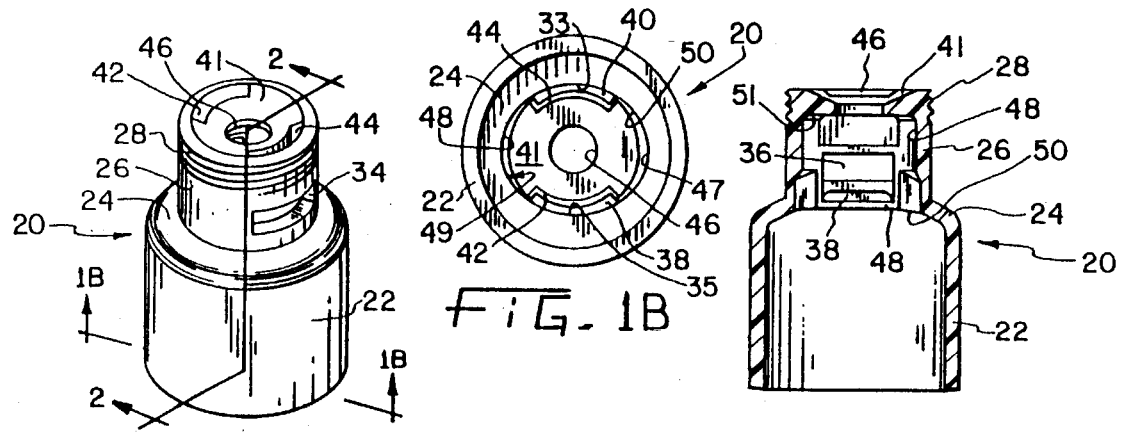
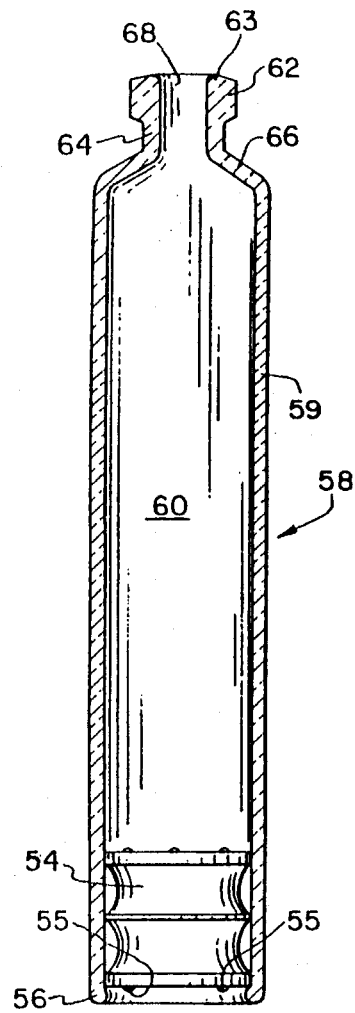

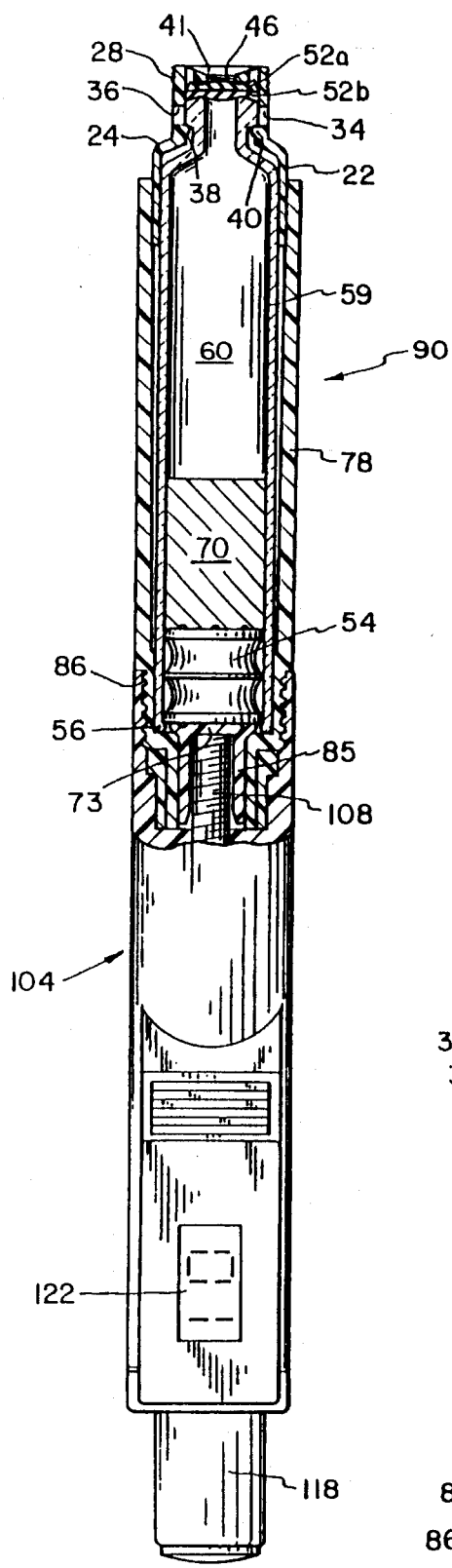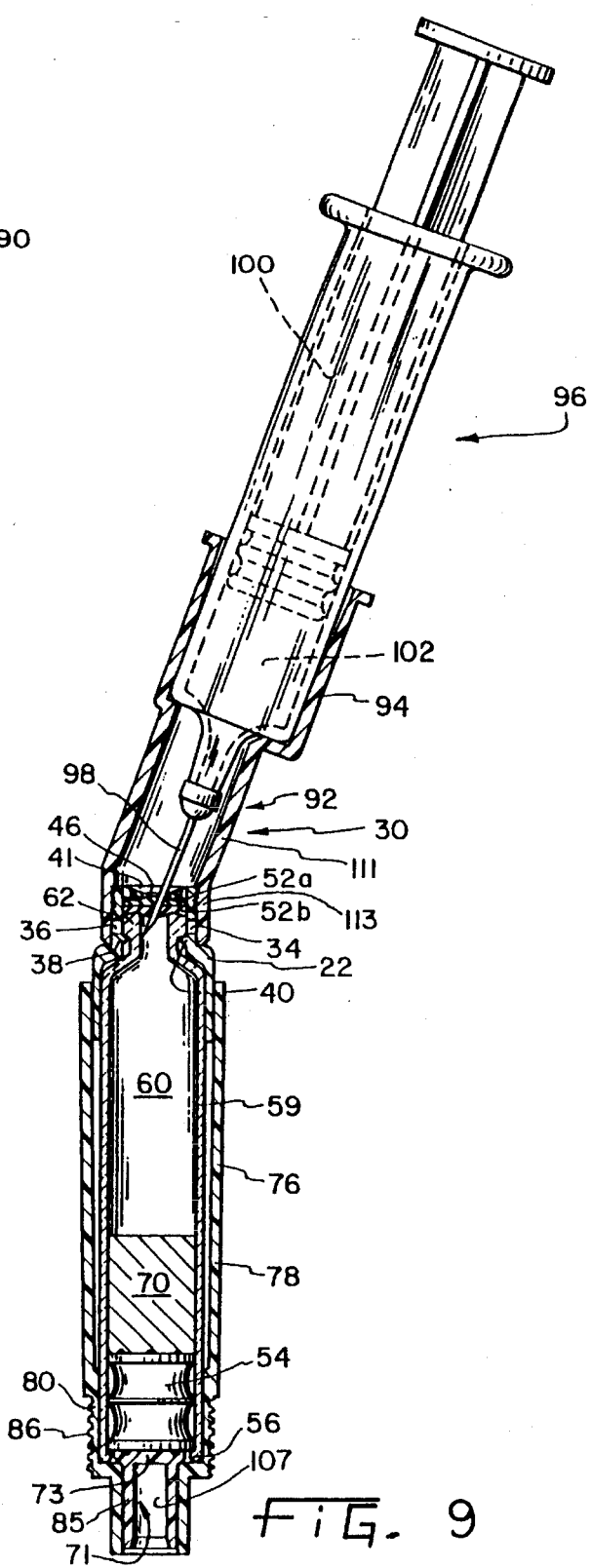

CARTRIDGE ASSEMBLY FOR A LYOPHILIZED COMPOUND FORMING A DISPOSABLE PORTION OF AN INJECTOR PEN AND METHOD FOR SAME

This is a division of application Ser. No. 08/031,683, filed Mar. 15, 1993 now U.S. Pat. No. 5,334,162.

BACKGROUND OF THE INVENTION

The present invention relates to the sealing and dispensing of pharmaceuticals and, more particularly to the sealing and dispensing of a lyophilized drug in a cartridge assembly.

In current technology, drugs or compounds manufactured for various injections are generally encapsulated in sterile glass cartridges. The glass cartridges characteristically have a sealed end with the other end of the cartridge generally having a restricted opening in the form of a neck having a circumferential flange. The opening can be closed off with a rubber membrane held into place with an aluminum seal crimped therearound. Where the drug or compound is to be later dispensed either directly from the cartridge or in a dispensing device such as a pen dispenser, the cartridge includes at the end opposite the restricted opening, an open end generally having a rubber plunger closing the open end. The rubber plunger also acts as a piston to force the drug or compound contained within the cartridge out of the restricted opening into which there has generally been inserted a cannula, by action of a plunger rod exerting axial pressure upon the rubber plunger.

cartridges for use with dispenser devices or pens as described above are generally known in the prior art. U.S. Pat. No. 4,936,833 Sams, shows a typical glass cartridge having an open end with a plunger therein, and an opposite end including a restricted opening sealed with a rubber membrane and crimped metal collar. The cartridge is insertable into a housing forming a part of a dispenser pen, with a cap for receiving a two ended cannula. Typical of these device are U.S. Pat. No. 4,883,472 Michel, and U.S. Pat. No. 4,973,318 Holm et al.

Lyophilized drugs or compounds are currently being utilized as the basis for injectionable compounds, such as human growth hormone (HGH), insulin, and the like. Lyophilization is the rapid freezing of a material at a very low temperature followed by rapid dehydration by sublimination in a high vacuum. The lyophilized compound is generally contained in a glass vial or cartridge. However, the process described above is not suitable for lyophilized compounds which are moisture and oxygen sensitive. When the moisture is removed from the compound during lyophilization, the oxygen in the glass cartridge containing a lyophilized drug must be replaced with nitrogen after the lyophilization process. This step of replacing the oxygen with nitrogen is termed nitrogen overlay and is accomplished within the lyophilizing chamber (freeze dryer).

One technique is to lyophilize the drugs or compounds in rubber stoppered glass vials. During lyophilization of the compounds in the glass vials, the rubber stopper used to close the vial is partially seated in the neck of the vial. The moisture which is removed from the compound during lyophilization is vented out through grooves or slots formed in the rubber stopper. As a general method of closing the vials, the shelves of the lyophilization chamber vertically move together to press the rubber stopper down into the vial, until the vents in the stopper are well inside the neck opening of the vial. An aluminum seal is then crimped about a flange on the neck of the vial.

The use of aluminum as a crimping seal for the rubber stopper is not, however, preferred due to the possibility of aluminum dust or particles contaminating the compound during the initial crimping, reconstitution, or administration processes. In addition, such processes as above are not well suited for efficient lyophilization.

Thus, it is desired to eliminate the aluminum crimping seal as well as provide an easier method of assuredly allowing lyophilization of a compound and sealing the same.

In order to administer a lyophilized compound, it is necessary to reconstitute the compound prior to administration with a suitable diluent. Reconstitution is accomplished by using a syringe with a needle to withdraw the diluent from a separate vial and inject it into the vial containing the lyophilized compound. The vial containing the lyophilized compound is placed in a holder during reconstitution. Because the cartridge is filled with the lyophilized compound and nitrogen, addition of the diluent produces extra pressure within the cartridge which creates the possibility of forcing the plunger out of the cartridge. Having the plunger forced out of the cartridge during reconstitution would undesirably result in a total loss of the compound.

During reconstitution, the diluent injected from the syringe into the cartridge directly impinges upon the lyophilized compound which causes the lyophilized compound to foam. The foam undesirably creates extra head space within the cartridge such that the proper amount of diluent is not mixed with the compound, resulting in an improper diluent to compound ratio. In order to alleviate this, one must wait for the foam to subside.

A patient needle is then attached to the disc sealed end of the cartridge which thus allows the compound to be injected. Current injector pens dispense a selectable amount of drug depending on the required dosage. A plunger mechanism, including a plunger rod, pushes against the plunger in the cartridge. After each injection, the plunger mechanism and plunger rod retract during a resetting function of the injector pen. However, complete disengagement of the plunger rod from the plunger mechanism during retraction is highly undesirable, and can render the injector pen inoperative.

Because of the expanding use of pen dispensers or injectors utilizing cartridges for the administration of injectionable compounds, it is desired to provide a lyophilized compound in an improved cartridge suitable for use in an injector pen.

SUMMARY OF THE INVENTION

The present invention, in one form thereof, provides a method of lyophilizing a compound in a glass cartridge and sealing the same utilizing a closure cap with a seal, and encapsulating the same into a cartridge assembly.

A method of lyophilizing and sealing an injectionable product within a cartridge is provided which includes, providing a cartridge having a neck defining a first opening therein, and a second opening therein distal the first opening, the neck including a circumferential radially outwardly extending flange adjacent the first opening, inserting a plunger in the second opening, and inserting the product to be lyophilized into the cartridge. Further, there is provided a cap having a cylindrical portion and a seal, the cylindrical portion including an open bottom receivable over the neck, the cap including a top having an opening therein for receipt of a needle therethrough, at least one vent circumferentially disposed in the cap, and a deformable ledge in the cap extending radially inwardly from the cylindrical portion axially below the vent, the seal being axially disposed between the vent and the top so as to block the top opening. The cap is then placed onto the neck such that the deformable ledge rests upon the neck flange and the vent is in communication with the neck opening, after which the cartridge with the cap is placed in a lyophilizing chamber, wherein the product is lyophilized, and the cap is closed by exerting a downward pressure upon the cap such that the deformable ledge yieldably snaps around the neck flange to be lockingly retained thereunder, the vent is closed from communication with the neck opening, and the seal is compressed into sealing engagement with the neck opening by downward pressure exerted by the top thereby providing an air impermeable barrier between the top opening and the neck opening.

The method of sealing a lyophilized product within a cartridge is further characterized by providing a sleeve having a first open end and a radially inwardly extending circumferential ledge into which the cartridge is placed. The cartridge is axially seated against the ledge and the sleeve is permanently attached to the cap.

A plunger rod tip having a plunger head is received in the sleeve between the plunger and ledge such that the plunger head is axially adjacent the plunger.

The present invention, in one form thereof, provides a cartridge assembly containing a lyophilized drug having a cartridge, a cap and seal, a cartridge sleeve, and a plunger mechanism forming a disposable portion of an injector pen.

A cartridge assembly for holding a lyophilized drug and forming a disposable part of an injection pen comprises a cartridge having a plug in one end and a neck on another end, the cartridge including a circumferentially extending flange about the neck, the neck defining an opening therein, a cap disposed about the neck, the cap having a first cylindrical portion including an open bottom received over the neck, a top having an opening therein for receipt of a needle therethrough, and a deformable ledge extending radially inwardly from the first cylindrical portion and lockingly retained under the neck flange. A resilient seal is disposed in the cap between the neck opening and the top opening forming an impermeable barrier therebetween, with a sleeve radially disposed about and permanently attached to the cartridge.

Further, the sleeve is permanently attached to the cap, and includes a first cylindrical portion adapted to receive the cartridge and a second cylindrical portion axially below the first cylindrical portion and concentric therewith, and a radially inward circumferentially extending ledge defined at the junction of the first and second cylinder for axially retaining the one end of the cartridge.

In one form thereof the present invention provides a method and apparatus for reconstituting a lyophilized compound, the lyophilized compound contained within an interior space defined by an inner wall of the cartridge having an inlet at one end thereof. The method comprising the step of injecting a diluent into the cartridge via the inlet such that the diluent impinges on and runs down the inner wall of the cartridge to thereby contact the compound, whereby foaming of the compound is alleviated.

A connector is releasably secured to the inlet end of the cartridge and adapted to receive and hold a syringe containing a diluent. The connector has a first portion defining a longitudinal axis which forms an oblique angle with the longitudinal axis of the cartridge. The syringe is supported by the connector at the oblique angle whereby the diluent is injected into the cartridge via the inlet at the oblique angle so that the diluent impinges on the wall of the cartridge.

The cartridge of the present invention is adapted to be used with an injector pen apparatus for administering a drug. The apparatus comprises a cartridge assembly having a cartridge with a movable plunger therein and an inlet on one end thereof. The cartridge assembly includes a rod tip having a recess therein and disposed axially adjacent the plunger and is adapted to exert pressure upon the plunger for dispensing the drug from the cartridge. An injector pen is releasably engaged with the cartridge assembly, the pen including a movable rod adapted to engage the recess of the rod tip in order to move the rod tip during dispensing of the drug. For injection of the drug, the rod retracts a known distance away from the plunger within the recess of the rod tip. The rod is then advanced towards the plunger a selected number of discrete increments as determined by the number of clicks depending on the desired dosage to be administered. During injection, the rod then advances the known distance towards the plunger which causes the plunger to advance the distance determined by the amount of discrete increments. The rod then retracts the known distance within the travel length of the rod tip.

It is an advantage of the present invention that the closure cap does not require close tolerances in cartridge manufacture.

It is another advantage of the present invention in that the cartridge, closure cap with seal, and cartridge case with plunger form a tamper resistant package.

It is yet another advantage of the present invention that the cartridge assembly prevents the plunger from outwardly moving during shipment of the cartridge assembly and during reconstitution of the lyophilized drug contained therein.

It is further an advantage of the present invention that foaming of the lyophilized compound is prevented during reconstitution thereof.

It is still another advantage of the present invention in that the cartridge assembly is protected from breakage.

It is also an advantage of the present invention that container integrity for the drug is increased.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 1A is a perspective view of the closure cap according to an aspect of the present invention;

FIG. 1B is a bottom view of the closure cap taken along line 1B—1B of FIG. 2;

FIG. 2 is a sectional elevational view of the closure cap taken along line 2—2 of FIG. 1A;

FIG. 3 is an elevational cutaway view of the glass cartridge and plunger;

FIG. 4 is an elevational cutaway view of the glass cartridge with plunger seated on a shelf with the closure cap in an open condition;

FIG. 5 is an elevational cutaway view of the glass cartridge with plunger seated on a shelf with the closure cap in a closed position;

FIG. 8 is a partial cutaway view of the cartridge assembly according to an embodiment of the present invention installed on a dispensing pen unit;

FIG. 9 is an elevational cutaway view of the cartridge assembly during reconstitution;

Figure 6:
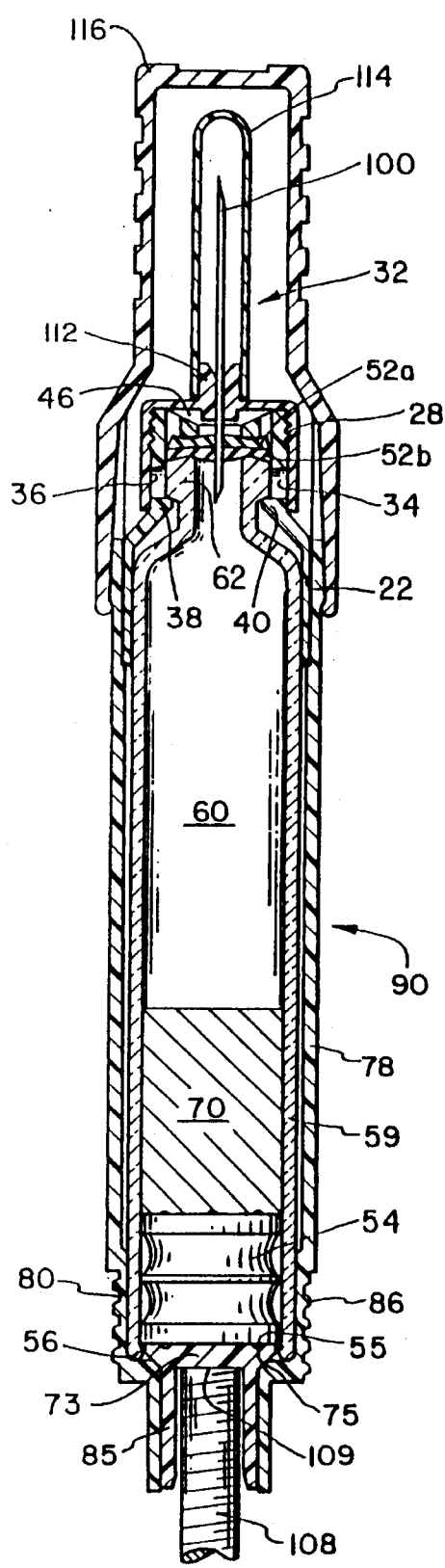
FIG. 6 is an elevational cutaway view of a cartridge assembly with user needle and cap.

Corresponding reference characters indicate corresponding parts throughout the several views. The exemplifications set out herein illustrate a preferred embodiment of the invention, in one form thereof, and such exemplifications are not to be construed as limiting the scope of the invention in any manner.

DESCRIPTION OF THE PREFERRED EMBODIMENT

Referring now to FIGS. 1A, 1B, and 2, there is shown a closure or lyophilization cap 20 in accordance with an aspect of the present invention. In general, cap 20 is preferably made of an injection molded plastic, although other suitable materials as known in the art may be utilized with the cap thus fabricated accordingly. Cap 20 has a cylindrical bottom portion or skirt 22 of a given axial length and inner radius sufficient to extend about at least a portion of a lyophilization cartridge. As further described hereinbelow, bottom portion or skirt 22 stabilizes cap 20 when placed onto cartridge 58 in the open position during lyophilization, and serves as a guide during closing of the cap. Cylindrical bottom portion 22 has a slightly upwardly and inwardly sloping annular shoulder 24, with a cylindrical top portion or neck 26 disposed axially above and inwardly concentric to cylindrical bottom portion 22. Top portion 26 includes threads 28 circumferentially formed on the outer upper periphery thereof which are adapted to threadedly receive a connector 30 (FIGS. 9 and 10) and needle assembly 32 (FIG. 6) both of which are described in more detail hereinbelow. Formed in cylindrical top portion 26 below threads 28 are two diametrically opposed circumferentially extending rectangular openings 34 and 36 which serve to vent moisture from cartridge 58 (FIGS. 3–5) during lyophilization and which allow the oxygen purge and nitrogen overlay process to occur thereafter.

As best seen in FIG. 1B, extending radially inward from wall 33 and 35 just below openings 34 and 36 are two ledges 38 and 40 having a circumferential length roughly corresponding to openings 34 and 36. As will be described in more detail hereinbelow, ledges 34 and 36 serve the dual function of allowing closure cap 20 to be seated upon cartridge 58 thus permitting communication between openings 34, 36 and the interior 60 of cartridge 58, and of snapping around and under circumferential flange 62 of cartridge neck 64 upon closing cap 20. Ledges 38 and 40 are sized and shaped so as to reduce the closing pressure required during the closing process, described hereinbelow, and to minimize the amount of cap deformation as closure is taking place. Cap 20 includes a top 41 which downwardly slopes from the outer upper edge of cylindrical top portion 26 terminating at an aperture 46 adapted to expose a seal 52 and receive a needle as described in detail hereinbelow. Two arched slots 42 and 44 are disposed in top portion 41 each axially upwardly of a respective side opening 34, 36. Arched slots 42 and 44 are formed during the molding process in order to achieve the undercut ledges 38 and 40 sufficiently large enough to allow for variations in the diameters of cartridge flanges.

Defined at the level 50 of ledges 38, 40 interior to cap 20 are walls 33, 35, 47, and 48 that define an oval or elliptic surface 49 whose major axis is transverse to an axis defined by connecting the middle of side openings 34, 36 or ledges 38, 40 such that each longitudinal end of oval or ellipse 49 is located 90° from each ledge 38 and 40. Walls 47 and 48 are thinner than walls 33 and 35 carrying ledge 38 and 40 so that as the ledges are forced outwardly during seating of cap 20, walls 47, 48 can move inward to accommodate such outward movement of walls 33 and 35 carrying ledges 38, 40. However, the thicker walls 33, 35 provide adequate support for ledges 38, 40 to prevent dislodgement of cap 20 from cartridge 58. This reduces the pressure required to close cap 20 onto cartridge 58 after lyophilization and nitrogen purge in order to prevent stress fractures in cap 20 and allow for more cartridges to be closed at one time. Such elliptical configuration of walls 33, 35, 47 and 48 extends the entire inner axial length thereof.

A circumferential ridge 51 is disposed about the interior of cylindrical top portion 26 axially below and adjacent top 41. Ridge 51 permits seal 52, such as for instance a laminated, two-piece rubber seal, to be seated therein without dislodging for efficient covering of opening 46.

The structure of cap 20 assists the natural deformation that occurs during the closure process. Thus, as cap 20 is pressed onto cartridge 58, ledges 38, 40 spring outward to allow it to go over and then underneath neck flange 62 (see FIG. 3).

What has thus been described hereinabove is a cap adapted to be seated upon a cartridge during lyophilization and which effectively and positively closes upon the cartridge to securely hold a disc seal about the opening. The cap is designed for efficient lyophilization and optimal nitrogen sealability while requiring only a minimum amount of closure force.

The process of lyophilizing a compound in cartridge 58 utilizing the hereinabove described cap 20 will now be described in conjunction with FIGS. 3–5. First, it should be noted that the various parts are sterilized prior to placement in the freeze dryer so that the compound to be lyophilized will be free from contamination. Secondly, it should be noted that a plurality of cartridges (up to 6000 or more) are generally lyophilized at one time. The cartridges are held in blocks defining a matrix of rows and columns of cartridges with the blocks placed in a freeze dryer chamber between movable shelve units, described hereinbelow. A typical configuration is 2000 per layer with three layers. The general structure of the various elements will also be described when introduced during the description of the process.

Cartridge 58 is manufactured of glass and consists of a tube portion 59 defining an inner chamber 60 and which openly terminates at one end with a circumferential inwardly bulbous lip 56. The other end of tube 59 includes an upwardly and inwardly sloping shoulder portion 66, a reduced diameter neck 64 and a rim 63 having circumferential flange 62 having a circumferential radius greater than that of neck 64. The end of cartridge 58 including flange 62 defines an opening 68 which communicates with inner chamber 60. Recessed neck 64 has a diameter that is smaller than shoulder 66. A rubber plunger 54 having knobs 55 is first disposed in the end having lip 56 just far enough into cartridge 58 such that the end of plunger 54 is adjacent lip 56. This is to keep the inside of cartridge 58 sterile after lyophilization.

Cartridge 58 with plunger 54 is placed between shelves 72 and 74 in the freeze dryer (not shown) with the liquid compound or drug 70 to be lyophilized contained therein. Cap 20 having rubber disc seal 52 disposed therein is placed over flange 62 defining a first or open position, the placement of cap 20 onto cartridge 58 occurring either before placement of cartridge 58 into the freeze dryer or thereafter. However, compound 70 is placed into cartridge 58 before the placement of cap 20 upon flange 62. Seal 52 is preferably a laminate of two different materials, the upper material 52a being a good sealing material, with the bottom material 52b being a good product contact material such as, for example, a normal butyl rubber compound. However, any resilient sealing material may be utilized which provides a good product contact material on the bottom and a good sealing material on the top.

Referring specifically to FIG. 4, cap 20 is designed such that ledges 38 and 40 rest on top of flange 62. In the first or open position a part of cylindrical bottom portion 22 circumferentially surrounds an upper part of tube 59 thereby serving as a stabilizer for cap 20 and a guide when cap 20 is moved to the second or closed position. Seal 52 is held in an elevated position above cartridge opening 68, while side openings 34 and 36 are above opening 68 thus allowing communication between the ambient atmosphere and inner chamber 60 of cartridge 58. At this point lyophilization begins.

Lyophilization, or freeze drying, which is represented in FIG. 4 as an upward and outward arrow, purges the moisture from compound 70 such that a waterless compound is left. Although the arrow is shown exiting only one side opening 36, it should be understood that the moisture is vented out through both openings 34, 36 during lyophilization. Once the moisture has been vented out of cartridge 58, oxygen is purged from the lyophilization chamber and thus cartridge 58. A nitrogen overlay process is then initiated. The nitrogen overlay process is represented in FIG. 4 as an inward and downward arrow entering from side opening 34, but as is the case for the venting of moisture and oxygen purge, the nitrogen enters through both side openings 34 and 36 to fill the entire inner space 60 of cartridge 58 not occupied by the now lyophilized compound 70. The nitrogen overlay process is used where the lyophilized compound is oxygen sensitive, as, for example, HGH.

At this point and referring now to FIG. 5, shelves 72 and 74 move vertically together in order to close cap 20 onto neck 64. As described above, cap 20 includes an oval or elliptical indentation 47 and inner wall 48 which allows cap 20 and ledges 38 and 40 to deform and flex so that ledges 38 and 40 snap around neck flange 62 as cap 20 is downwardly pressed by the pressure exerted by closing shelves 72 and 74. A force of only about 10–12 lbs. is thus necessary to effect closure of cap 20 about neck 64 and neck flange 62. Once in place, cylindrical bottom portion 22 extends about an upper part of tube 59, while ledges 38 and 40 prohibits removal of cap 20 by extending under neck flange 62 between the flange and sloped neck section 66.

Upon closure of cap 20, seal 52 is compressed between the top of rim and downwardly sloped cap top 41 to effect a positive, airtight seal between the ambient atmosphere and the nitrogen and lyophilized compound within cartridge 58. There is no need for a crimp seal, while both the lyophilization and closure processes are completed within the lyophilizing chamber. At this point, the sealed cartridge may be removed from the lyophilizing chamber. A cake or plug of compound 70 is thus sealed within a nitrogen filled cartridge.

Figure 7:
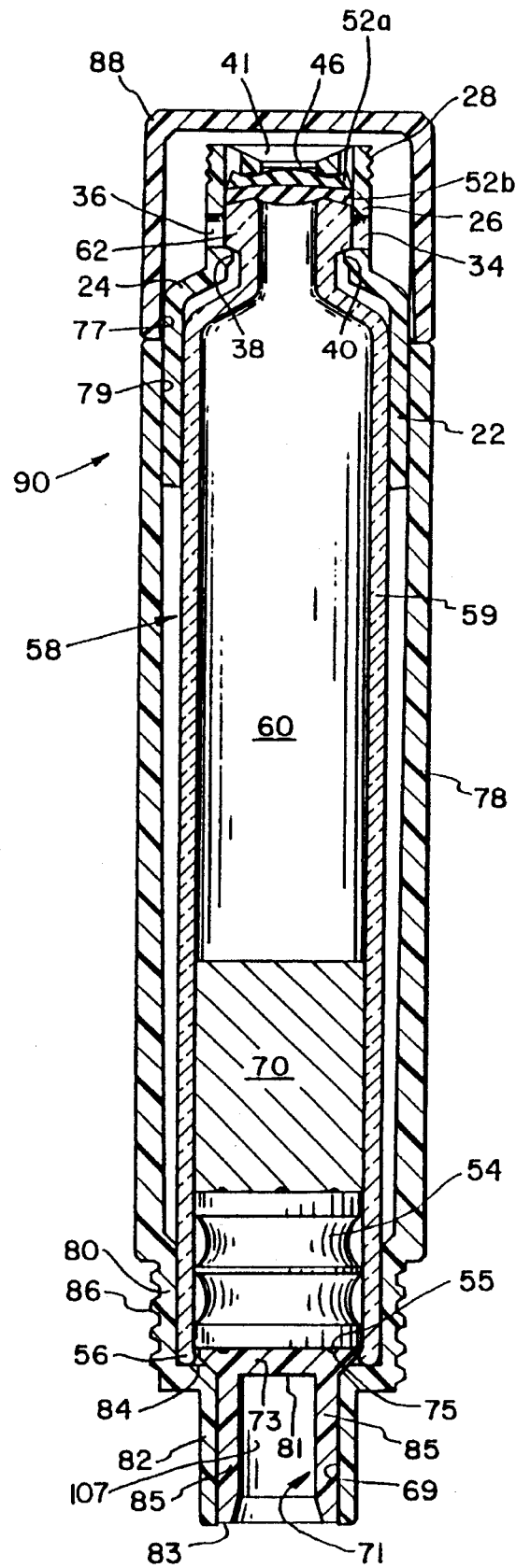
FIG. 7 is an elevational cutaway view of the cartridge assembly according to an embodiment of the present invention.

After lyophilization, and referring to FIG. 7, sealed cartridge 58 is then placed into a cartridge sleeve, barrel, or retainer 76 through an opening 77 in one end thereof. The sleeve is preferably made from a suitable plastic or other material which provides protection for the glass cartridge.

Sleeve 76 comprises a first tubular portion 78 having an inner diameter 79 of sufficient size such that a segment of first tubular portion 78 radially surrounds or overlaps cylindrical bottom portion 22 of cap 20. At this junction, sleeve 76 is attached or sealed to cap 20 by use of a solvent, adhesive bond, snap fit, sonic weld, or the like, such that cartridge 58 is retainingly held in sleeve 76. Sleeve 76 also includes a second tubular portion 80 having a smaller diameter than first tubular portion 78 such that tube 59 of cartridge 58 is inwardly circumjacent the inner diameter thereof. Threads 86 on the outer periphery of second tubular portion 80 permit sleeve 76 to be received onto an injection pen device.

Sleeve 76 further comprises a third tubular portion 82 having a smaller diameter than second tubular portion 80, the second tubular portion defining an annular stop or ledge 84 at the junction of second and third tubular portions 80 and 82. Stop 84 supports lip 56 such that tube 59 is supported thereon. A sleeve cap 88 optionally may fit about the top of the cartridge assembly 90 to further protect the seal assembly. Thus, the cartridge is securely held by and contained within sleeve 76 and ready for reconstitution before administration and placement into an injector pen dispenser.

Sleeve 76 has a smaller diameter opening 69 at the other end through which extends a plunger rod tip 71. Rod tip 71 is placed within sleeve 76 before insertion of cartridge 58, and has a circular rod head 73, slightly less than the inner diameter of cartridge 58, on one end of a hollow cylindrical body 85. The lower portion of rod head 73 is seated against sleeve ledge 84 and is of sufficient diameter such that rod tip 71 is retained in sleeve 76. Rod tip body 85 is of sufficient length to axially extend from head 73 to the axial end of third tubular portion 82.

Cylindrical body 85 defines an axially elongated cylindrical recess or bore 107. Recess 107 defined by cylindrical body 85 between bottom portion 81 of rod head 73 and end portion 83 is of a specific axial length, for example, eight and nine tenths millimeters (8.9 mm). The upper surface of circular rod head 73 of rod tip 71 abuts plunger 54 and includes an annular groove 75 into which knobs 55 of plunger 54 are seated. As pressure is applied to plunger 54 in order to administer the reconstituted compound, plunger 54, being an elastomeric or rubber, has a tendency to deform during compression. However, because of its resiliency, plunger 54 returns to its original shape, which sequence could cause weeping of the liquid from around the plunger. Rod head 73 serves to distribute the load exerted by the compression of rod tip 71 in order to eliminate weeping from about plunger 54 which could occur as a result of uneven or localized compression of plunger 54. Annular groove 75 retains knobs 55 to prevent lateral deformation, which could cause weeping.

Figure 10:
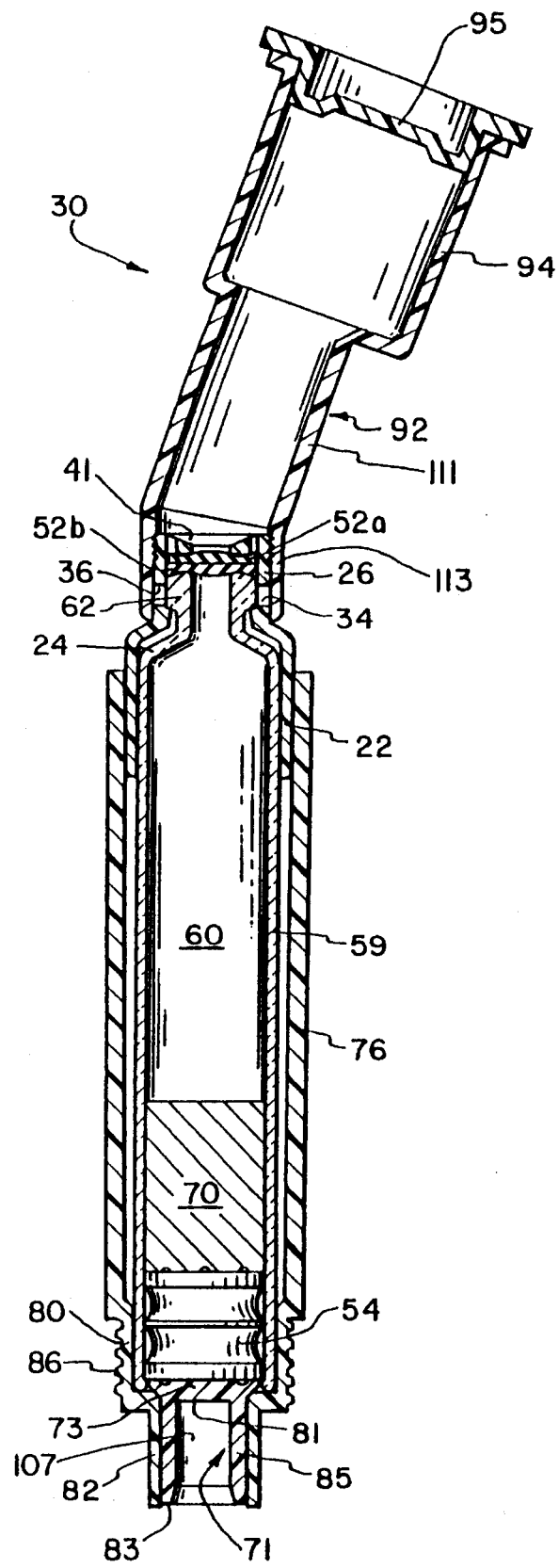
FIG. 10 is an elevational cutaway view of the cartridge assembly with connector and connector lid before insertion into a dispensing pen and reconstitution.

As shown in FIG. 10, a connector 30 is threadedly attached to threads 28 of cap 20. This occurs after placement of cartridge 58 in sleeve 76 and attachment of cap 20 thereto. Connector 30, introduced hereinabove, is threadedly attached to threads 28 of cap 20 and includes an angled first section 92 and a larger diameter second section 94. First section 92 is tubular in shape and includes an upper section 111 and, at its lower end, an angled neck portion 113 having mating threads for threads 28. Neck portion 113 is essentially concentric and defines a common axis with cartridge 58. Upper section 111 defines an axis which thus forms an oblique angle with the axis of neck portion 113. Larger diameter portion 94 is eccentric with upper section 111 of first section 92. A common axis is also defined between upper section 111 and portion 94.

A lid 95 is snapped in place over cylindrical second section 94 thereby sealing the space there between. This entire assembly is then sterilized so that the contents of the cartridge and the area about the disc seal is sterile for later reconstitution and administration.

Reconstitution is performed as shown in FIG. 9. After removal of connector lid 95, connector 30 is thus adapted to receive a syringe 96 in second section 94 which supports syringe 96 but allows needle 98 to enter hole 46 and penetrate seal 52 such that only a small section of needle 98 extends into cartridge 58. During reconstitution, the action produced by the force of moving diluent upon the lyophilized cake (e.g. HGH) triggers a reaction which causes the HGH cake to become agitated and foam. Foaming undesirably creates air bubbles, thereby limiting the amount of diluent that can be added to the cartridge. This can result in improper dilution ratios of the lyophilized compound. Furthermore, once the foam subsides, too large a headspace is created within the cartridge.

According to one aspect of the present invention, connector 30 is obliquely angled as described above such that needle 98 is oriented toward and preferably in close proximity to wall 58 and injects diluent 102 down the side of the interior wall of cartridge 58 in order to prevent foaming of the compound during the reconstitution process. Side impingement of the diluent reduces the velocity of the diluent as it travels toward and onto the HGH cake. This indirect administration of the diluent by causing the diluent to impinge on the inner side wall of cartridge 58 and then run down around and into the HGH prevents foaming.

Syringe 96 is prefilled with a suitable diluent 102, and as plunger 100 of syringe 96 forces fluid into the lyophilized cartridge, the nitrogen in cartridge 58 is compressed. Releasing syringe plunger rod 100 while holding the syringe above the cartridge, allows the pressure in the cartridge to equilibrate by venting the nitrogen into the syringe, leaving the diluent in the cartridge to mix with the lyophilized drug. The syringe is then removed and discarded.

A transfer needle 32, such as those manufactured by Becton-Dickinson, can then be threadedly attached to cap 20 where connector 30 was attached during reconstitution. This is shown in FIG. 6. The typical transfer needle 32 is a double-ended needle 110, which extends in one direction through hole 46 in top 41 and seal 52 to communicate with the reconstituted drug within the cartridge. Needle 110 is secured in a needle housing 112 and protected during nonuse by a plastic cap 114 and needle assembly protector cap 116.

Referring in particular now to FIG. 8, cartridge assembly 90 is threadedly attached to an injector pen 104, such as that manufactured by Disetronic AB of Burgdorf, Switzerland. A plunger rod 108 fits into recess 107 of rod tip 71 in order to effect ejection of the reconstituted drug from the cartridge. The inside length of rod tip 71 is adapted to retain the injector pen plunger rod 108 during the injector pen's compression and retraction stroke. When the drug is to be administered to the patient, the needle assembly 32 as shown in FIG. 6 is attached to cap 20 as described hereinabove.

Figure 11:
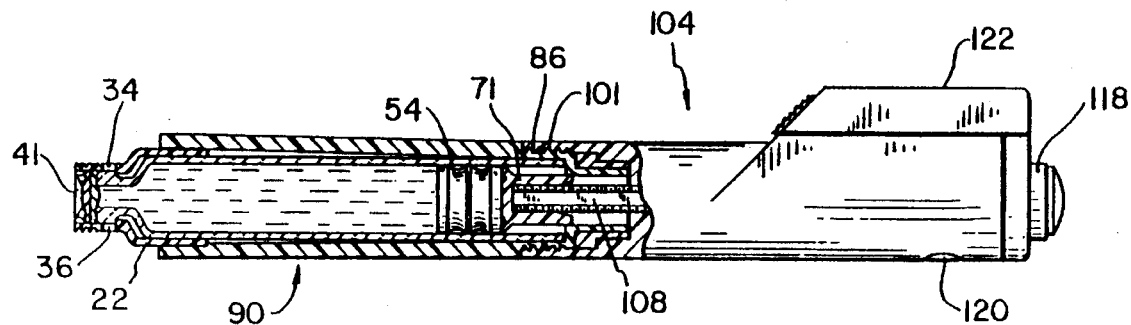
FIG. 11 is a partial cutaway view of the cartridge assembly installed on a dispensing pen.
Figure 12:
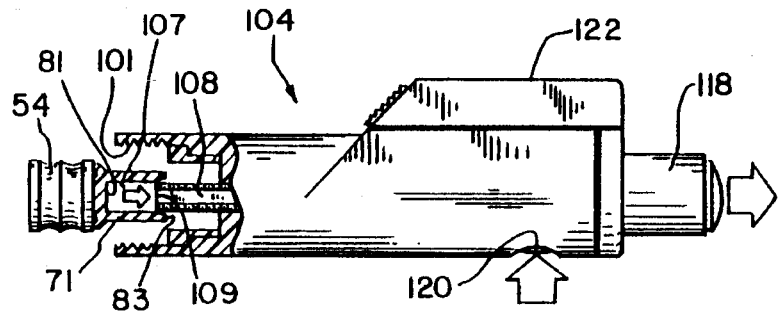
FIGS. 12–14 are partial cutaway views of the plunger and rod mechanism as utilized with the dispensing pen illustrating the injection process.
Figure 13:
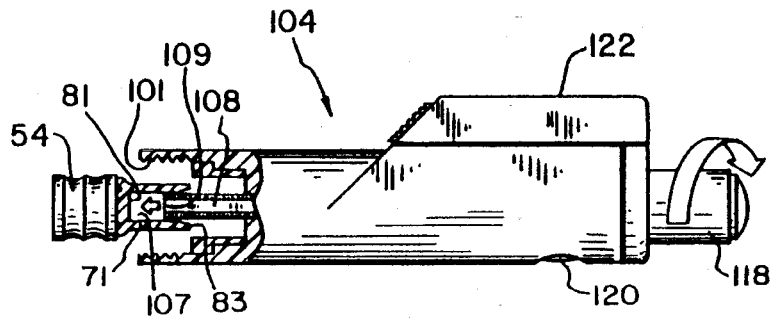
Figure 14:
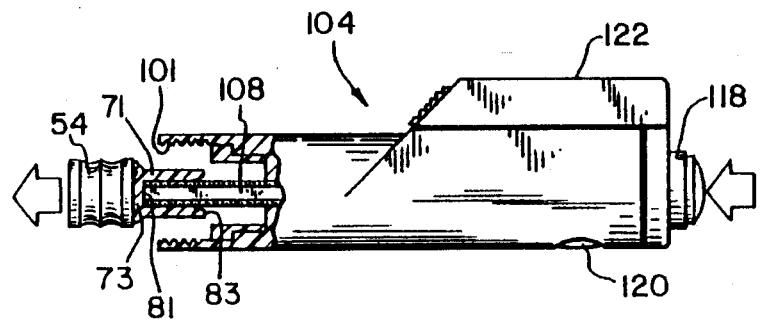

One such type of injector pen is shown in FIG. 11 and its operation described in conjunction with additional FIGS. 12–14. Referring to FIG. 11, cartridge assembly 90 is shown connected to injector pen 104 via complementary threads 86, 101. Injector pen 104 includes a pen rod 108, a dose knob 118 and a release button 120. Pen rod 108 fits into a suitable mechanism within pen body 106 for providing the injector function as described below in conjunction with FIGS. 12–14.

It should be noted with respect to FIGS. 12–14 that for simplicity of discussion and understanding of an aspect of the present invention that only rubber plunger 54 and plunger rod tip 71 of the cartridge assembly are shown in relationship to pen 104 and, in particular pen rod 108. To load the assembly for the first time, release button 120 is pushed such that dose knob 118 pops out. At this point, pen rod 108 retracts a known, or predetermined distance, for example 8.1 millimeters away from plunger 54 within recess 107. Dose knob 118 is then turned until dose knob 118 stops which causes pen rod 108 to travel forward towards plunger 54 a set maximum amount for purging. Upon retraction, pen rod 108 cooperates with rod tip 71 in that pen rod 108 does not travel any more than 8.1 millimeters out of the 8.9 mm (for example) recess 107 of the rod tip 71. End 109 of plunger rod 108 thus never retracts past a plane defined at the end 83 of rod tip 71 perpendicular to an axis of elongation of rod tip 71. Thus, rod 108 never disengages from recess 107.

The rod tip, being an integral part of the housing for the cartridge assembly prevents the plunger 54 in the cartridge from being forced out during the reconstitution process. Further, rod tip 71 allows movement required by the pen's plunger rod 108 during dose setting and injection. When dose knob 118 is pushed in, the unit purges 95 percent of all of the air in the cartridge in order to obtain a proper head space. Thus, after reconstitution, and initial purging, the injector pen assembly is ready for the administration process as shown in FIG. 11.

In order to administer the drug to the patient, release button 120 is pressed which causes dose knob 118 to pop out and correspondingly cause pen rod 108 to retract the 8.1 mm maximum travel distance within the 8.9 mm rod tip 71, each action being depicted by respective arrows in FIG. 12. As noted hereinabove, end 109 never retracts past end 83. Dose knob 118 is then turned through so many clicks, the clicks corresponding to volume units of dosage depending on the required amount of dosage. Each click corresponding to a given volume of injectionable liquid. This is depicted in FIG. 13. As the required number of clicks are set via dose knob 118, pen rod 108 correspondingly moves forward an amount equal to the number of clicks, with each click correspondingly moving pen rod 108 a predetermined distance being coordinated with a set dosage amount.

As shown in FIG. 14, when dose knob 118 is depressed, pen rod 108 thus contacts rod head 73 of rod tip 71 to administer the drug by traveling the 8.1 mm distance. Upon retraction of pen rod 108 in order to administer another dose, pen rod 108 retracts the set 8.1 mm distance within the 8.9 mm recess 107. This ensures that pen rod 108 never comes out of rod tip 107.

The process as depicted in FIGS. 12–14 is repeated at the prescribed times until all of the drug has been administered. A dose indication device 122 is provided to visually indicate the dosage set by dose knob 118. Such dose indication may be purely mechanical in nature or electronic, such as an LCD display.

Once the entire drug has been administered to the patient, the entire cartridge assembly and patient needle assembly is then discarded. The injector pen is then ready for another cartridge assembly 90.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for reconstituting a lyophilized compound, comprising:

providing a lyophilized compound contained within an interior space defined by an inner wall of a cartridge having an inlet at one end thereof and a plunger at an opposite end thereof;

attaching a connector to the inlet end of the cartridge, the connector having a neck portion coaxial with a longitudinal axis of the cartridge and a tubular first portion connected to said neck portion, said first portion having an interior space and defining an axis along a longitudinal length thereof, the axis of the first portion forming an oblique angle relative to the axis of the cartridge;

placing a syringe having a needle and containing the diluent into the interior space of the first portion, such that the needle is oriented toward the inner wall of the cartridge; and injecting a diluent from the syringe into the cartridge via the inlet such that the diluent impinges on and runs down the inner wall of the cartridge before contacting the lyophilized compound whereby foaming of the compound is prevented.

2. A method of reconstituting a lyophilized compound comprising:

providing a lyophilized compound contained within an interior space defined by an essentially annular inner wall of a cylindrical cartridge, the cartridge including an inlet on one end thereof and a plunger on an opposite end thereof and defining an axis extending through the inlet along the longitudinal length thereof;

removably attaching a connector on the inlet end of the cartridge, the connector defining an open-ended cavity for receipt of a syringe containing the diluent, the connector including a tubular angled portion for receiving and angularly positioning the diluent syringe relative to the cartridge, the angled portion defining an axis along a longitudinal length thereof, the axis of the angled portion forming an oblique angle relative to the axis of the cartridge;

placing the syringe containing the diluent into the tubular angled portion such that a needle of the syringe extends through the inlet at the oblique angle; and injecting the diluent into the cartridge through the needle whereby the diluent is caused to impinge upon and run down the inner wall of the cartridge before contacting the lyophilized compound.

3. An apparatus for reconstituting a lyophilized drug contained within an inner space of a cartridge comprising:

a cartridge having an inlet on one end thereof, a plunger on the opposite end and containing a lyophilized drug, said cartridge defining a longitudinal axis extending through the inlet, a connector releasably secured to the inlet end of the cartridge and adapted to receive and hold a syringe containing a diluent, the connector having a neck portion coaxial with the axis of the cartridge and having a tubular first portion defining a longitudinal axis which forms an oblique angle with the longitudinal axis of the cartridge, the syringe adapted to be supported by the connector at the oblique angle whereby the diluent is injected into the cartridge via the inlet at the oblique angle.

4. The apparatus of claim 3, wherein said neck portion is received on the inlet end of the cartridge, the connector further including a tubular second portion eccentric with said first portion, said second portion having a larger diameter than the diameter of said first portion and adapted to retain and support the syringe.

5. The apparatus of claim 4 including a lid on said tubular second portion for sealing the interior of said connector.

* * * * *